US00PP20537P2

(12) United States Plant Patent
Blom

(10) Patent No.: US PP20,537 P2
(45) Date of Patent: Dec. 8, 2009

(54) ***ECHINACEA* PLANT NAMED 'MERINGUE'**

(50) Latin Name: *Echinacea purpurea*
Varietal Denomination: Meringue

(76) Inventor: Arie Blom, Waterbieslaan 110, 3452 AR, Vleuten (NL)

( * ) Notice: Subject to any disclaimer, the term of this patent is extended or adjusted under 35 U.S.C. 154(b) by 0 days.

(21) Appl. No.: 12/217,739

(22) Filed: Jul. 7, 2008

(51) Int. Cl.
*A01H 5/00* (2006.01)

(52) U.S. Cl. ..... Plt./428
(58) Field of Classification Search ..... Plt./428
See application file for complete search history.

*Primary Examiner*—Annette H. Para
*Assistant Examiner*—Louanne C Krawczewicz Myers
(74) *Attorney, Agent, or Firm*—C. A. Whealy

(57) ABSTRACT

A new and distinct cultivar of *Echinacea* plant named 'Meringue', characterized by its upright, columnar and compact plant habit; moderately vigorous growth habit; freely basal branching habit; and large inflorescences with light yellow green-colored ray florets and yellow green-colored disc florets.

2 Drawing Sheets

Botanical designation: *Echinacea purpurea.*
Cultivar denomination: 'Meringue'.

BACKGROUND OF THE INVENTION

The present invention relates to a new and distinct cultivar of *Echinacea* plant, botanically known as *Echinacea purpurea*, and hereinafter referred to by the name 'Meringue'.

The new *Echinacea* is a product of a planned breeding program conducted by the Inventor in IJsselstein and Zuidwolde, The Netherlands. The objective of the breeding program is to create new compact *Echinacea* cultivars with attractive inflorescence form and floret coloration.

The new *Echinacea* originated from a cross-pollination in IJsselstein, The Netherlands in July, 2004 made by the Inventor of a proprietary selection of *Echinacea purpurea*, identified as code number Ec 301-36, not patented, as the female, or seed, parent with a proprietary selection of *Echinacea purpurea* identified as code number Ec 202-02, not patented, as the male, or pollen, parent. The new *Echinacea* was discovered and selected by the Inventor as a single flowering plant from within the progeny of the stated cross-pollination grown in a controlled greenhouse environment in Zuidwolde, The Netherlands in July, 2006.

Asexual reproduction of the new *Echinacea* by micropropagation a controlled greenhouse environment in The Netherlands since September, 2006, has shown that the unique features of this new *Echinacea* are stable and reproduced true to type in successive generations.

SUMMARY OF THE INVENTION

Plants of the new *Echinacea* have been observed under all possible environmental conditions. The phenotype may vary somewhat with variations in environment such as temperature and light intensity, without, however, any variance in genotype.

The following traits have been repeatedly observed and are determined to be the unique characteristics of 'Meringue'. These characteristics in combination distinguish 'Meringue' as a new and distinct cultivar of *Echinacea:*

1. Upright, columnar and compact plant habit.
2. Moderately vigorous growth habit.
3. Freely basal branching habit.

4. Large inflorescences with light yellow green-colored ray florets and yellow green-colored disc florets.

Plants of the new *Echinacea* differ from plants of the female parent selection in the following characteristics:

1. Plants of the new *Echinacea* are more compact than plants of the female parent selection.
2. Plants of the new *Echinacea* have stronger stems than plants of the female parent selection.
3. Plants of the new *Echinacea* and the female parent selection differ in ray floret color as plants of the female parent selection have pink-colored ray florets.

Plants of the new *Echinacea* differ from plants of the male parent selection in the following characteristics:

1. Plants of the new *Echinacea* are shorter than plants of the male parent selection.
2. Plants of the new *Echinacea* are more freely branching than plants of the male parent selection.

Plants of the new *Echinacea* can be compared to plants of *Echinacea purpurea* 'Coconut Lime', disclosed in U.S. Plant Pat. No. 18,617. In side-by-side comparisons conducted in Zevenhuizen, The Netherlands, plants of the new *Echinacea* differed from plants of 'Coconut Lime' in the following characteristics:

1. Plants of the new *Echinacea* were shorter than plants of 'Coconut Lime'.
2. Ray florets of plants of the new *Echinacea* were lighter in color than ray florets of plants of 'Coconut Lime'.

BRIEF DESCRIPTION OF THE PHOTOGRAPHS

The accompanying photographs illustrate the overall appearance of the new *Echinacea*. The photographs show the colors as true as it is reasonably possible to obtain in colored reproductions of this type. Colors in the photographs may differ slightly from the color values cited in the detailed botanical description which accurately describe the colors of the new *Echinacea*.

The photograph on the first sheet comprises a side perspective view of a typical flowering plant of 'Meringue' grown in a container.

The photograph at the top of the second sheet is a close-up view of a typical inflorescence of 'Meringue'. The photograph at the bottom of the second sheet is a close-up view of a typical leaf of 'Meringue'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Zevenhuizen, The Netherlands during the autumn in an outdoor nursery and under conditions and practices which approximate those generally used in commercial *Echinacea* production. During the production of the plants, day temperatures ranged from 11° C. to 25° C. and night temperatures ranged from 3° C. to 15° C. Measurements and numerical values represent averages for typical flowering plants. Plants were one year from planting in containers when the photographs and description were taken.

Botanical classification: *Echinacea purpurea* 'Meringue'.

Parentage:

*Female parent.*—Proprietary selection of *Echinacea purpurea* identified as code number Ec 301-36, not patented.

*Male parent.*—Proprietary selection of *Echinacea purpurea* identified as code number Ec 202-02, not patented.

Propagation:

*Type.*—By micropropagation.

*Time to initiate roots.*—About one week at 25° C.

*Time to produce a rooted young plant.*—About five weeks at 21° C.

*Root description.*—Fine, fibrous; pale cream white in color.

*Rooting habit.*—Freely branching; moderately dense.

Plant description:

*Plant form/growth habit.*—Upright, columnar and compact plant habit; freely basal branching with about eight basal branches developing per plant. Moderately vigorous growth habit.

*Plant height.*—About 44.1 cm.

*Plant diameter or spread.*—About 20.9 cm.

*Basal branches.*—Length: About 24.4 cm. Diameter: About 4 mm. Internode length: About 3.9 cm. Aspect: Mostly upright. Strength: Strong. Texture: Pubescent; rough. Color: Close to 144A.

Foliage description:

*Arrangement.*—Alternate, simple.

*Length.*—About 8.2 cm.

*Width.*—About 2.7 cm.

*Shape.*—Narrowly ovate to ovate.

*Apex.*—Acute.

*Base.*—Attenuate, elongated.

*Margin.*—Entire to slightly sinuate.

*Texture, upper and lower surfaces.*—Pubescent; rough.

*Venation pattern.*—Pinnate.

*Color.*—Developing leaves, upper surface: Close to 137C. Developing leaves, lower surface: Close to 146B. Fully expanded leaves, upper surface: Close to 137A; venation, close to 145B. Fully expanded leaves, lower surface: Close to 146B; venation, close to 145A to 145B.

*Petiole length.*—About 2.8 cm.

*Petiole diameter.*—About 2 mm to 3 mm.

*Petiole texture, upper and lower surfaces.*—Sparsely pubescent.

*Petiole color, upper and lower surfaces.*—Close to 145A to 145B.

Inflorescence description:

*Appearance.*—Rotate single inflorescence form with ray and disc florets. Inflorescences positioned above the foliage on strong peduncles and face upright. About ten inflorescences per plant at a time. Inflorescences not persistent.

*Fragrance.*—None detected.

*Time to flower.*—Plants flower continuously from late June to mid-October in The Netherlands.

*Inflorescence longevity.*—Inflorescences maintain good substance for about three weeks on the plant.

*Inflorescence bud.*—Height: About 1.7 cm. Diameter: About 2.2 cm. Shape: Flattened globular. Color: Between 143A and 146A.

*Inflorescence size.*—Diameter: About 8.5 cm. Depth (height): About 5 cm. Disc diameter: About 5.7 cm. Receptacle height: About 8 mm. Receptacle diameter: About 1.2 cm. Receptacle color: Close to 155A.

*Ray florets.*—Length: About 3.5 cm. Width: About 9 mm. Shape: Oblanceolate. Apex: Praemorse. Base: Cuneate. Margin: Entire. Texture, upper and lower surfaces: Smooth, glabrous; longitudinally ridged. Number of ray florets per inflorescence: About 21 arranged in a single whorl. Aspect: Horizontal to reflexing. Color: When opening, upper surface: Close to 150D; towards the apex, close to 145D. When opening, lower surface: Close to 150D; towards the apex, close to 145C. Fully opened, upper surface: Between 150D and 157A, becoming closer to 145A to 145B with development; towards the apex, close to 145C. Fully opened, lower surface: Close to 150C, color becoming closer to 145A with development; towards the apex, close to 145A; towards the base, close to 145B.

*Disc florets.*—Length: About 2.2 cm. Diameter: About 3 mm. Shape: Tubular, enlarged; apices acute. Number of disc florets per inflorescence: About 450. Texture, upper and lower surfaces: Smooth, glabrous. Color: Immature, inner and outer surfaces: Close to 150C; towards the apex, close to 145A. Mature, inner and outer surfaces: Close to 150D; towards the apex, close to 150C.

*Receptacle spines.*—Quantity: One per disc floret. Shape: Acicular. Apex: Acute. Base: Attenuate. Texture: Smooth, glabrous. Color: Apex: Close to 22A. Mid-section: Close to 143A. Base: Close to 145C to 145D.

*Involucral bracts.*—Quantity per inflorescence: About 60 in about three whorls. Length: About 7 mm. Width: About 2 mm. Shape: Narrowly ovate. Apex: Acute. Base: Cuneate. Margin: Entire. Texture, upper surface: Smooth, glabrous. Texture, lower surface: Pubescent. Color, upper surface: Close to 137A to 137B. Color, lower surface: Close to 138B; towards the apex, close to 137B.

*Peduncles.*—Length: About 16 cm. Diameter: About 4 mm. Strength: Strong. Aspect: Mostly upright. Texture: Pubescent; rough. Color: Close to 144A.

*Reproductive organs.*—Androecium: Quantity per floret: About two. Filament length: About 3 mm. Filament color: Close to 165C. Anther shape: Oblong, short. Anther length: About 1 mm. Anther color: Close to 165A to 165B. Pollen amount: None observed. Gynoecium: Quantity per floret: One. Pistil length: About 8 mm. Stigma shape: Decurrent.

Stigma color: Close to 150B to 150C. Style length: About 6 mm. Style color: Close to 150D. Ovary color: Close to 157D. Fruits/seeds: Fruit and seed development have not been observed.

Disease/pest resistance: Plants of the new *Echinacea* have not been shown to be resistant to pathogens and pests common to *Echinacea*.

Garden performance: Plants of the new *Echinacea* have exhibited good tolerance to rain and wind, have been observed to tolerate temperatures ranging from about −20° C. to about 40° C.

It is claimed:

1. A new and distinct *Echinacea* plant named 'Meringue' as illustrated and described.

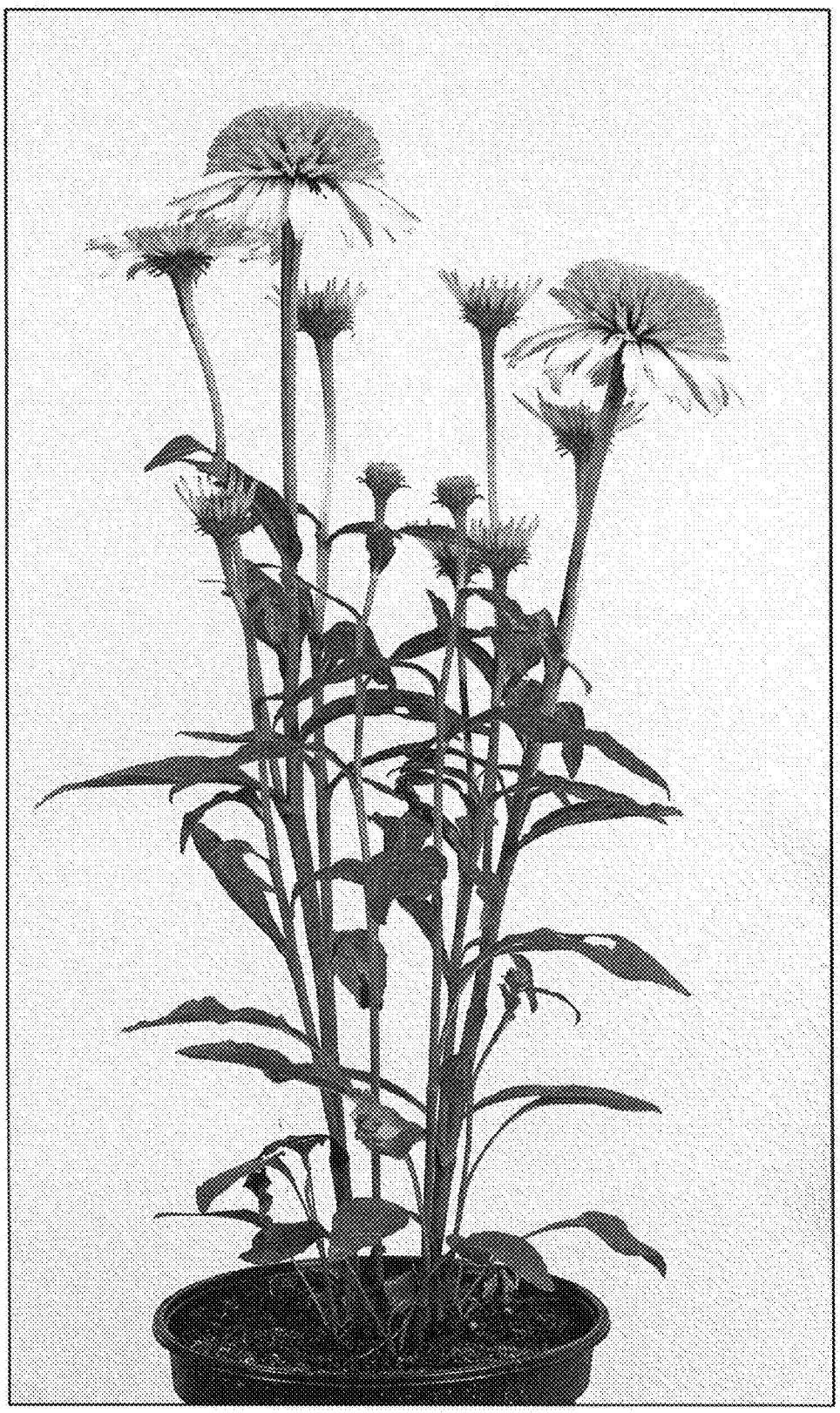

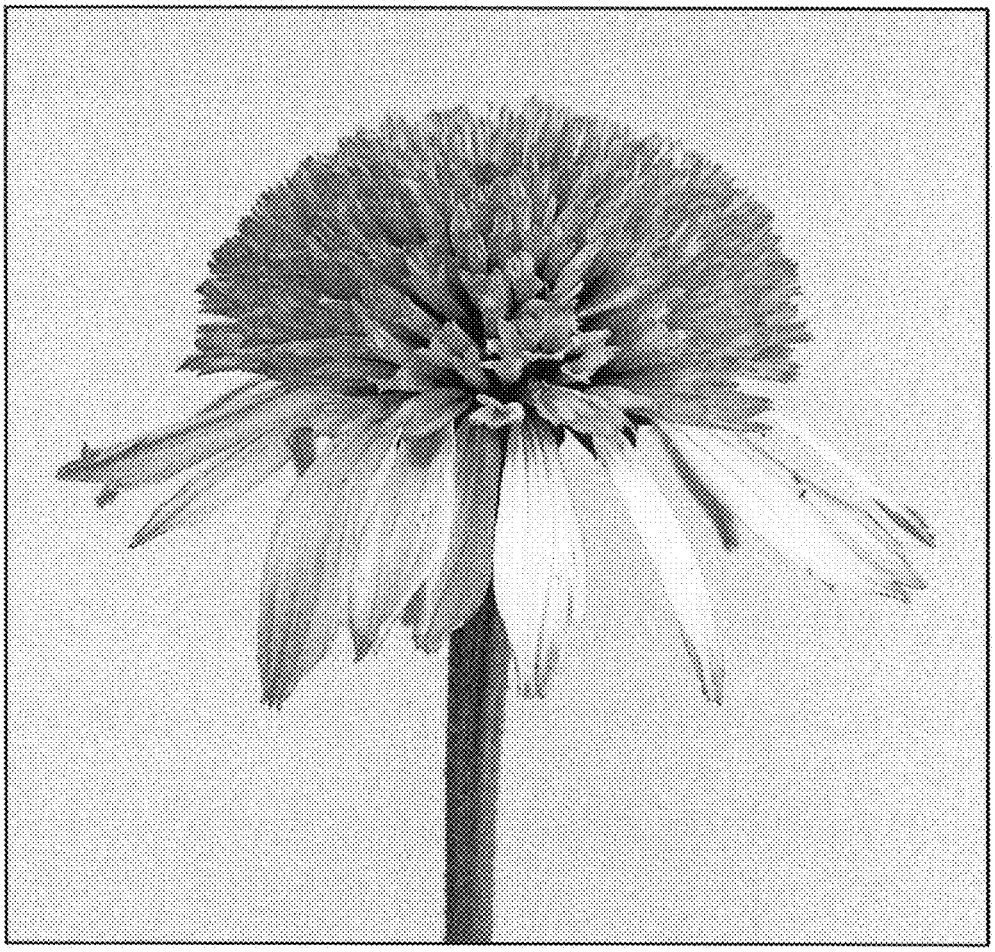
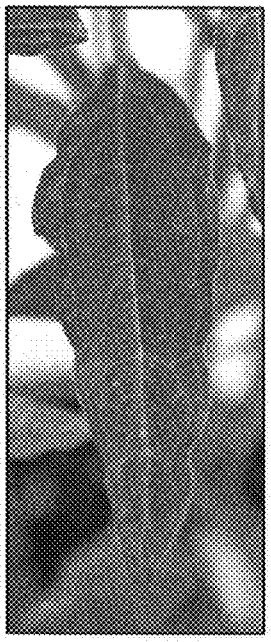

* * * * *